(12) United States Patent
Mault

(10) Patent No.: US 6,607,387 B2
(45) Date of Patent: Aug. 19, 2003

(54) SENSOR SYSTEM FOR DIAGNOSING DENTAL CONDITIONS

(75) Inventor: James R. Mault, Evergreen, CO (US)

(73) Assignee: Healthetech, Inc., Golden, CO (US)

(*) Notice: Subject to any disclaimer, the term of this patent is extended or adjusted under 35 U.S.C. 154(b) by 0 days.

(21) Appl. No.: 10/040,016

(22) Filed: Oct. 26, 2001

(65) Prior Publication Data

US 2002/0061495 A1 May 23, 2002

Related U.S. Application Data

(60) Provisional application No. 60/244,309, filed on Oct. 30, 2000.

(51) Int. Cl.$^7$ ................................................. A61C 5/00
(52) U.S. Cl. ....................................................... 433/215
(58) Field of Search ........................... 433/27, 29, 215, 433/72; 600/532, 543, 530; 424/9.7, 9.71; 422/84, 85

(56) References Cited

U.S. PATENT DOCUMENTS

| | | | |
|---|---|---|---|
| 2,630,798 A | 3/1953 | White et al. | 128/2.07 |
| 2,826,912 A | 3/1958 | Kritz | 73/194 |
| 2,831,348 A | 4/1958 | Kritz | 73/861.28 |
| 2,838,399 A | 6/1958 | Vogel, Jr. | 99/48 |
| 2,869,357 A | 11/1959 | Kritz | 73/32 |
| 2,911,825 A | 11/1959 | Kritz | 73/194 |
| 2,920,012 A | 1/1960 | Sanders et al. | 167/51.5 |
| 3,213,684 A | 10/1965 | Seaton et al. | 73/190 |
| 3,220,255 A | 11/1965 | Scranton et al. | 73/204 |
| 3,250,270 A | 5/1966 | Bloom | 128/2.07 |
| 3,306,283 A | 2/1967 | Arp | 128/2.07 |
| 3,523,529 A | 8/1970 | Kissen | 128/2.07 |
| 3,527,205 A | 9/1970 | Jones | 128/2.08 |
| 3,681,197 A | 8/1972 | Smith | 195/63 |
| 3,726,270 A | 4/1973 | Griffis et al. | 128/2.08 |
| 3,799,149 A | 3/1974 | Rummel et al. | 128/2.07 |
| 3,814,091 A | 6/1974 | Henkin | 128/188 |
| 3,834,375 A | 9/1974 | Sanctuary et al. | 128/2.07 |

(List continued on next page.)

FOREIGN PATENT DOCUMENTS

| | | |
|---|---|---|
| DE | 198 10 476 | 9/1998 |
| EP | 0459647 A2 | 12/1991 |
| EP | 0 712 638 | 12/1995 |

(List continued on next page.)

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise".

British Journal Of Anaesthesia, vol. 49, 1977 London (GB) pp. 575–587, J. A. Bushman et al. "Closed Circuit Anaesthesia".

(List continued on next page.)

*Primary Examiner*—Carey E. O'Connor
(74) *Attorney, Agent, or Firm*—Gifford, Krass, Groh, Sprinkle, Anderson & Citkowski, P.C.

(57) ABSTRACT

A sensor system for diagnosing dental conditions includes a sensor unit which is in contact with an oral fluid such as saliva or gas, and which is operative to provide detectable signals indicative of at least two of hydrogen ion concentration, hydroxyl ion concentration, calcium, phosphate, sulfur, sulfur containing compounds, nitrogen containing compounds, microbial metabolites, and microbes. The system includes a signal processor which is in communication with the sensor unit and which operates to provide a processed signal indicative of one or more dental conditions. The signal processor transmits the processed signal to a storage and display device which displays a user detectable diagnostic message indicative of a dental condition, or suggestive of a remedial action.

27 Claims, 4 Drawing Sheets

U.S. PATENT DOCUMENTS

| | | | |
|---|---|---|---|
| 3,895,630 A | 7/1975 | Bachman | 128/2.07 |
| 3,938,551 A | 2/1976 | Henkin | 137/613 |
| 3,962,917 A | 6/1976 | Terada | 73/204 |
| 3,967,690 A | 7/1976 | Northcutt | 177/25 |
| 3,972,038 A | 7/1976 | Fletcher et al. | 340/189 M |
| 3,979,480 A | 9/1976 | Radici et al. | 260/857 F |
| 3,991,304 A | 11/1976 | Hillsman | 235/151.33 |
| 4,003,396 A | 1/1977 | Fleischmann | 137/83 |
| 4,008,712 A | 2/1977 | Nyboer | 128/2.1 Z |
| 4,051,847 A | 10/1977 | Henkin | 128/145.6 |
| 4,078,554 A | 3/1978 | Lemaitre et al. | 128/2.08 |
| 4,100,401 A | 7/1978 | Tutt et al. | 235/92 MT |
| 4,101,071 A | 7/1978 | Brejnik et al. | 235/92 MT |
| 4,113,039 A | 9/1978 | Ozaki et al. | 177/25 |
| 4,117,834 A | 10/1978 | McPartland et al. | 128/2 S |
| 4,151,668 A | 5/1979 | Hugerford | 40/495 |
| 4,159,416 A | 6/1979 | Brejnik et al. | 235/92 MT |
| 4,186,735 A | 2/1980 | Henneman et al. | 128/201.25 |
| 4,188,946 A | 2/1980 | Watson et al. | 128/204.22 |
| 4,192,000 A | 3/1980 | Lipsey | 364/415 |
| 4,197,857 A | 4/1980 | Osborn | 600/531 |
| 4,200,094 A | 4/1980 | Gedeon et al. | 128/201.13 |
| 4,211,239 A | 7/1980 | Raemer et al. | 128/716 |
| 4,212,079 A | 7/1980 | Segar et al. | 364/900 |
| 4,221,224 A | 9/1980 | Clark | 128/718 |
| 4,221,959 A | 9/1980 | Sessler | 377/13 |
| 4,224,952 A | 9/1980 | Sidorenko et al. | 128/782 |
| 4,230,108 A | 10/1980 | Young | |
| 4,244,020 A | 1/1981 | Ratcliff | 364/413 |
| 4,318,447 A | 3/1982 | Northcutt | 177/25 |
| 4,321,674 A | 3/1982 | Krames et al. | 364/413 |
| 4,334,540 A | 6/1982 | Preti et al. | 128/630 |
| 4,341,867 A | 7/1982 | Johansen | 435/189 |
| 4,347,233 A | 8/1982 | Yamauchi et al. | 424/7 |
| 4,353,375 A | 10/1982 | Colburn et al. | 128/782 |
| 4,359,057 A | 11/1982 | Manzella | 128/718 |
| 4,366,873 A | 1/1983 | Levy et al. | 177/25 |
| 4,368,740 A | 1/1983 | Binder | 128/718 |
| 4,380,802 A | 4/1983 | Segar et al. | 364/900 |
| 4,386,604 A | 6/1983 | Hershey | 128/718 |
| 4,387,777 A | 6/1983 | Ash | 177/43 |
| 4,423,792 A | 1/1984 | Cowan | 177/25 |
| 4,425,805 A | 1/1984 | Ogura et al. | 73/861.29 |
| 4,440,177 A | 4/1984 | Anderson et al. | 600/532 |
| 4,444,201 A | 4/1984 | Itoh | 128/716 |
| 4,463,764 A | 8/1984 | Anderson et al. | 600/532 |
| 4,566,461 A | 1/1986 | Lubell et al. | 128/668 |
| 4,571,682 A | 2/1986 | Silverman et al. | 364/413 |
| 4,572,208 A | 2/1986 | Cutler et al. | 128/718 |
| 4,575,804 A | 3/1986 | Ratcliff | 364/715 |
| 4,577,710 A | 3/1986 | Ruzumna | 177/245 |
| 4,582,795 A | 4/1986 | Shibuya et al. | 435/34 |
| 4,598,700 A | 7/1986 | Tamm | 128/671 |
| 4,608,995 A | 9/1986 | Linnarsson et al. | 128/713 |
| 4,619,269 A | 10/1986 | Cutler et al. | 128/719 |
| 4,629,015 A | 12/1986 | Fried et al. | 177/25 |
| 4,648,396 A | 3/1987 | Raemer | 600/534 |
| 4,650,218 A | 3/1987 | Hawke | 283/67 |
| 4,658,832 A | 4/1987 | Brugnoli | 600/532 |
| 4,686,624 A | 8/1987 | Blum et al. | 364/415 |
| 4,709,331 A | 11/1987 | Barkett et al. | 364/413 |
| 4,719,923 A | 1/1988 | Hartwell et al. | 128/663 |
| 4,731,726 A | 3/1988 | Allen, III | 364/416 |
| 4,753,245 A | 6/1988 | Gedeon | 128/718 |
| 4,756,670 A | 7/1988 | Arai | 417/43 |
| 4,757,453 A | 7/1988 | Nasiff | 364/415 |
| 4,781,184 A | 11/1988 | Fife | 128/205.12 |
| 4,793,362 A | 12/1988 | Tedner | 128/734 |
| 4,796,182 A | 1/1989 | Duboff | 364/413.29 |
| 4,796,639 A | 1/1989 | Snow et al. | 600/532 |
| 4,803,625 A | 2/1989 | Fu et al. | 364/413.03 |
| 4,807,169 A | 2/1989 | Overbeck | 364/715.01 |
| 4,823,808 A | 4/1989 | Clegg et al. | 128/773 |
| 4,850,371 A | 7/1989 | Broadhurst et al. | 600/532 |
| 4,853,854 A | 8/1989 | Behar et al. | 364/413.01 |
| 4,855,942 A | 8/1989 | Bianco | 364/561 |
| 4,855,945 A | 8/1989 | Sakai | 364/709.2 |
| 4,856,531 A | 8/1989 | Merilainen | 600/532 |
| 4,880,014 A | 11/1989 | Zarowitz et al. | 128/734 |
| 4,891,756 A | 1/1990 | Williams, III | 364/413.29 |
| 4,894,793 A | 1/1990 | Ikemoto et al. | 364/709.03 |
| 4,895,163 A | 1/1990 | Libke et al. | 128/734 |
| 4,909,259 A | 3/1990 | Tehrani | 600/531 |
| 4,911,175 A | 3/1990 | Shizgal | 128/734 |
| 4,911,256 A | 3/1990 | Attikiouzel | 177/25.16 |
| 4,914,959 A | 4/1990 | Mylvaganam et al. | 73/861.28 |
| 4,917,108 A | 4/1990 | Mault | 600/531 |
| 4,924,389 A | 5/1990 | Gerbaulet et al. | 364/413.29 |
| 4,947,862 A | 8/1990 | Kelly | 128/734 |
| 4,951,197 A | 8/1990 | Mellinger | 364/413.2 |
| 4,954,954 A | 9/1990 | Madsen et al. | 364/413.29 |
| 4,955,946 A | 9/1990 | Mount et al. | 600/532 |
| 4,965,553 A | 10/1990 | DelBiondo, II et al. | 340/573 |
| 4,966,155 A | 10/1990 | Jackson | 128/671 |
| 4,976,951 A | 12/1990 | Rosenberg et al. | 424/7.1 |
| 4,986,268 A | 1/1991 | Tehrani | 128/204 |
| 4,998,018 A | 3/1991 | Kurahashi et al. | 250/343 |
| 5,007,429 A | 4/1991 | Treatch et al. | 128/677 |
| 5,012,411 A | 4/1991 | Policastro et al. | 364/413.06 |
| 5,019,974 A | 5/1991 | Beckers et al. | 364/413.02 |
| 5,022,406 A | 6/1991 | Tomlinson | 128/719 |
| 5,033,561 A | 7/1991 | Hettinger | 177/25.16 |
| 5,038,773 A | 8/1991 | Norlien et al. | 128/205.23 |
| 5,038,792 A | 8/1991 | Mault | 128/718 |
| 5,042,500 A | 8/1991 | Norlien et al. | 600/532 |
| 5,042,501 A | 8/1991 | Kenny et al. | 600/532 |
| 5,060,506 A | 10/1991 | Douglas | 73/24.1 |
| 5,060,655 A | 10/1991 | Rudolph | 128/716 |
| 5,060,656 A | 10/1991 | Howard | 128/718 |
| 5,063,937 A | 11/1991 | Ezenwa et al. | 128/723 |
| 5,068,536 A | 11/1991 | Rosenthal | 250/341 |
| 5,069,220 A | 12/1991 | Casparie et al. | 128/719 |
| 5,072,737 A | 12/1991 | Goulding | 128/718 |
| 5,077,476 A | 12/1991 | Rosenthal | 250/341 |
| 5,081,871 A | 1/1992 | Glaser | 73/863.23 |
| 5,086,781 A | 2/1992 | Bookspan | 128/734 |
| 5,095,900 A | 3/1992 | Fertig et al. | 128/207.14 |
| 5,095,913 A | 3/1992 | Yelderman et al. | 128/719 |
| 5,117,674 A | 6/1992 | Howard | 73/31.07 |
| 5,119,825 A | 6/1992 | Huhn | 600/529 |
| 5,178,155 A | 1/1993 | Mault | 128/718 |
| 5,179,958 A | 1/1993 | Mault | 128/718 |
| 5,188,109 A | 2/1993 | Saito | 128/635 |
| 5,203,344 A | 4/1993 | Scheltinga | 128/734 |
| 5,214,966 A | 6/1993 | Delsing | 73/861.28 |
| 5,233,520 A | 8/1993 | Kretsch et al. | 364/413.29 |
| 5,233,996 A | 8/1993 | Coleman et al. | 600/529 |
| 5,263,491 A | 11/1993 | Thornton | 128/774 |
| 5,275,161 A | 1/1994 | Graves et al. | 128/635 |
| 5,280,429 A | 1/1994 | Withers | 364/413.15 |
| 5,282,473 A | 2/1994 | Braig et al. | 600/532 |
| 5,282,840 A | 2/1994 | Hudrlik | 607/28 |
| 5,285,794 A | 2/1994 | Lynch | 128/719 |
| 5,293,875 A | 3/1994 | Stone | 128/719 |
| 5,299,579 A | 4/1994 | Gedeon et al. | 600/532 |
| 5,303,712 A | 4/1994 | Van Duren | 600/529 |
| 5,306,144 A | 4/1994 | Hibst et al. | 433/29 |
| 5,307,263 A | 4/1994 | Brown | 364/413.09 |
| 5,309,921 A | 5/1994 | Kisner et al. | 600/532 |
| 5,326,973 A | 7/1994 | Eckerbom et al. | 250/343 |
| 5,335,667 A | 8/1994 | Cha et al. | 128/34 |

| Patent No. | Date | Inventor | Class |
|---|---|---|---|
| 5,355,879 A | 10/1994 | Brain | |
| 5,357,989 A | 10/1994 | Gathani | 132/321 |
| 5,363,857 A | 11/1994 | Howard | 600/531 |
| 5,372,141 A | 12/1994 | Gallup et al. | 128/734 |
| 5,387,164 A | 2/1995 | Brown, Jr. | 482/9 |
| 5,388,043 A | 2/1995 | Hettinger | 364/413.29 |
| 5,398,688 A | 3/1995 | Laniado | 128/660.02 |
| 5,398,695 A | 3/1995 | Anderson et al. | 600/532 |
| 5,402,796 A | 4/1995 | Packer et al. | 128/719 |
| 5,412,560 A | 5/1995 | Dennison | 364/413.01 |
| 5,412,564 A | 5/1995 | Ecer | 364/413.29 |
| 5,415,176 A | 5/1995 | Sato et al. | 128/734 |
| 5,419,326 A | 5/1995 | Harnoncourt | 128/660.02 |
| 5,421,344 A | 6/1995 | Popp | 128/734 |
| 5,425,374 A | 6/1995 | Ueda et al. | 600/532 |
| 5,449,000 A | 9/1995 | Libke et al. | 128/734 |
| 5,450,193 A | 9/1995 | Carlsen et al. | 356/301 |
| 5,454,721 A | 10/1995 | Kuch | 434/127 |
| 5,456,603 A | 10/1995 | Kowalyk et al. | 433/215 |
| 5,468,961 A | 11/1995 | Gradon et al. | 250/345 |
| 5,485,402 A | 1/1996 | Smith et al. | 364/566 |
| 5,492,674 A | 2/1996 | Meserol | 422/82.08 |
| 5,503,151 A | 4/1996 | Harnoncourt et al. | 128/660.02 |
| 5,542,420 A | 8/1996 | Goldman et al. | 128/630 |
| 5,570,697 A | 11/1996 | Walker et al. | 128/719 |
| 5,579,782 A | 12/1996 | Masuo | 128/734 |
| 5,611,351 A | 3/1997 | Sato et al. | 128/734 |
| 5,615,689 A | 4/1997 | Kotler | 128/734 |
| 5,628,313 A | 5/1997 | Webster, Jr. | 128/642 |
| 5,632,281 A | 5/1997 | Rayburn | 128/719 |
| 5,645,071 A | 7/1997 | Harnoncourt et al. | 128/719 |
| 5,647,370 A | 7/1997 | Harnoncourt | 128/725 |
| 5,673,691 A | 10/1997 | Abrams et al. | 128/630 |
| 5,676,132 A | 10/1997 | Tillotson et al. | 128/204.23 |
| 5,678,562 A | 10/1997 | Sellers | 128/710 |
| 5,678,571 A | 10/1997 | Brown | 128/898 |
| 5,691,927 A | 11/1997 | Gump | 364/709.01 |
| 5,704,350 A | 1/1998 | Williams, III | 128/630 |
| 5,705,735 A | 1/1998 | Acorn | 73/23.3 |
| 5,720,296 A | 2/1998 | Cha | 128/734 |
| 5,729,479 A | 3/1998 | Golan | 364/709.2 |
| 5,746,214 A | 5/1998 | Brown et al. | 128/693 |
| 5,754,288 A | 5/1998 | Yamamoto et al. | 356/301 |
| 5,788,643 A | 8/1998 | Feldman | 600/506 |
| 5,789,660 A | 8/1998 | Kofoed et al. | 73/23.3 |
| 5,796,009 A | 8/1998 | Delsing | 73/861.28 |
| 5,796,640 A | 8/1998 | Sugarman et al. | 364/709.02 |
| 5,800,360 A | 9/1998 | Kisner et al. | 600/532 |
| 5,810,722 A | 9/1998 | Heikkila | 600/300 |
| 5,816,246 A | 10/1998 | Mirza | 128/726 |
| 5,817,031 A | 10/1998 | Masuo et al. | 600/547 |
| 5,819,735 A | 10/1998 | Mansfield et al. | 128/630 |
| 5,822,715 A | 10/1998 | Worthington et al. | 702/19 |
| 5,827,179 A | 10/1998 | Lichter et al. | 600/300 |
| 5,831,175 A | 11/1998 | Fletcher-Haynes | 73/861.28 |
| 5,832,448 A | 11/1998 | Brown | 705/2 |
| 5,834,626 A | 11/1998 | DeCastro et al. | 73/23.3 |
| 5,836,300 A | 11/1998 | Mault | 600/532 |
| 5,836,312 A | 11/1998 | Moore | 128/897 |
| 5,876,351 A | 3/1999 | Rohde | 600/523 |
| 5,890,128 A | 3/1999 | Diaz et al. | 705/2 |
| 5,897,493 A | 4/1999 | Brown | 600/300 |
| 5,899,855 A | 5/1999 | Brown | 600/300 |
| 5,902,234 A | 5/1999 | Webb | 600/300 |
| 5,908,301 A | 6/1999 | Lutz | 434/236 |
| 5,910,107 A | 6/1999 | Iliff | 600/300 |
| 5,913,310 A | 6/1999 | Brown | 128/897 |
| 5,918,603 A | 7/1999 | Brown | 128/897 |
| 5,922,610 A | 7/1999 | Alving et al. | 436/116 |
| 5,932,812 A | 8/1999 | Delsing | 73/861.02 |
| 5,933,136 A | 8/1999 | Brown | 345/327 |
| 5,941,825 A | 8/1999 | Lang et al. | 600/449 |
| 5,951,300 A | 9/1999 | Brown | 434/236 |
| 5,957,858 A | 9/1999 | Micheels et al. | 600/532 |
| 5,974,124 A | 10/1999 | Schlueter, Jr. et al. | 379/106.02 |
| 5,981,300 A | 11/1999 | Möll et al. | 436/811 |
| 5,982,709 A | 11/1999 | Ladabaum et al. | 367/170 |
| 5,989,188 A | 11/1999 | Birkhoelzer et al. | 600/300 |
| 5,993,786 A | 11/1999 | Chow et al. | 424/49 |
| 5,997,476 A | 12/1999 | Brown | 600/300 |
| 6,010,459 A | 1/2000 | Silkoff et al. | 600/532 |
| 6,013,007 A | 1/2000 | Root et al. | 482/8 |
| 6,014,578 A | 1/2000 | Minoz | 600/350 |
| 6,024,281 A | 2/2000 | Shepley | 235/375 |
| 6,024,699 A | 2/2000 | Surwit et al. | 600/300 |
| 6,030,342 A | 2/2000 | Amano et al. | 600/301 |
| 6,032,676 A | 3/2000 | Moore | 128/898 |
| 6,040,531 A | 3/2000 | Miller-Kovach et al. | 177/25.16 |
| 6,042,383 A | 3/2000 | Herron | 434/238 |
| 6,044,843 A | 4/2000 | O'Neil et al. | 128/204.23 |
| 6,045,513 A | 4/2000 | Stone et al. | 600/508 |
| 6,067,989 A | 5/2000 | Katzman | 128/898 |
| 6,077,193 A | 6/2000 | Buhler et al. | 482/8 |
| 6,083,006 A | 7/2000 | Coffman | 434/127 |
| 6,095,949 A | 8/2000 | Arai | 482/4 |
| 6,095,985 A | 8/2000 | Raymond et al. | 600/513 |
| 6,101,478 A | 8/2000 | Brown | 705/2 |
| 6,122,536 A | 9/2000 | Sun et al. | 600/341 |
| 6,135,950 A | 10/2000 | Adams | 600/300 |
| 6,135,951 A | 10/2000 | Richardson et al. | 600/300 |
| 6,206,837 B1 | 3/2001 | Brugnoli | 600/529 |
| 6,264,615 B1 | 7/2001 | Diamond et al. | 600/530 |
| 6,309,360 B1 | 10/2001 | Mault | 600/531 |

FOREIGN PATENT DOCUMENTS

| | | |
|---|---|---|
| EP | 1013221 A1 | 2/1998 |
| GB | 2323292 | 9/1998 |
| WO | WO 96/40340 | 12/1996 |
| WO | 99/60925 | 2/1999 |

OTHER PUBLICATIONS

IEEE Transactions On Biomedical Engineering, vol. 35, No. 9, Sep. 1988, pp. 653–659, Capek et al., "Noninvasive Measurement of Caridac Output Using Partial CO2 ReBreathing".

Clinics In Chest Medicine (Review), vol. 10, 1989, pp. 255–264, Heigenhauser et al., "Measurement of Cardiac Output by Carbon Dioxide Rebreathing Methods".

Determination Of Nitric Oxide Levels By Fluorescence Spectroscopy, Gabor G. and Allon N. in Biochemical, Pharmacological, and Clinical Aspects of Nitric Oxide, edited by B. A. Weissman et al., Plenum Press, New York, 1995, p. 57.

SENSOR SYSTEM FOR DIAGNOSING DENTAL CONDITIONS

RELATED APPLICATION

This application claims priority of U.S. Provisional Patent Application No. 60/244,309 filed Oct. 30, 2000 and entitled "Dental Caries Reduction Using pH Monitoring".

FIELD OF THE INVENTION

The invention relates to dental health, in particular caries reduction. More particularly, the invention relates to a system for monitoring one or more dental conditions.

BACKGROUND OF THE INVENTION

Tooth enamel is formed from an insoluble form of calcium phosphate also known as hydroxyapatite. The enamel is formed in rods within a largely inorganic matrix material containing hydroxyapatite, some protein, and other compounds.

Oral bacteria form plaque deposits around the teeth. For example, the bacterium Streptococcus mutans (S. mutans) produces a molecule called glucan which helps the bacteria to bind themselves to the teeth and form plaque deposits. The plaque bacteria metabolize sugars and carbohydrates and as a byproduct form lactic acid. Tooth enamel is slightly soluble in the acidic environment which is produced. Calcium ions and phosphate ions enter solution, and so the enamel is stripped away, a process called demineralization. However, enamel may be remineralized between meals due to the action of calcium and phosphate ions present naturally in the saliva.

U.S. Pat. Nos. 5,275,161 and 5,628,313 describe systems and methods for diagnosing periodontal disease based upon the polarographic measurement of sulfide concentration in the mouth. U.S. Pat. No. 6,264,615 shows a similar method which is used to diagnose halitosis.

In U.S. Pat. No. 5,993,786, Chow et al. describe how calcium compounds such as calcium phosphate may be added to toothpaste, chewing gums, gels, etc., to enhance remineralization. The combination of calcium phosphate and fluoride ions is known to enhance remineralization. Other patents also describe remineralization products.

In U.S. Pat. No. 5,981,300, Moll et al. describe test kits for indicating the risk of dental caries. However, the kits include sugar-containing compositions.

In U.S. Pat. No. 5,306,144, Hibst et al. describe optical viewing of caries by e.g. irradiating with blue light and viewing red light (a reflection/fluorescence method).

In U.S. Pat. No. 5,357,989, Gathani describes dental floss impregnated with a pH indicator.

In U.S. Pat. No. 4,582,795, Shibuya describes enzymatic detection of oral microorganisms. However, the test is slow.

In U.S. Pat. No. 4,976,951, Rosenberg describes the localization of caries. However, this requires a slow incubation period.

All of the foregoing prior art approaches involve methods for detecting various dental conditions; however, these methods all rely upon the use of specific chemical compounds and/or test apparatus. However, none of the prior art approaches are operable to simultaneously measure a number of dental parameters and to provide a user detectable diagnostic message indicative of the state of the user's health. Furthermore, none of the prior art approaches are integratable with data storage and management devices such as a personal digital assistance (PDA), personal computer, central computer, or the like. As will be detailed hereinbelow, the present invention provides a monitoring system which can be integrated with personal health monitoring equipment such as an individual, handheld calorimeter, and can be further operable in connection with personal data storage devices. The system of the present invention operates to monitor parameters indicative of dental health, and is further operative to provide a user with a display which describes the state of the user's dental health and/or suggests corrective actions. These and other advantages of the invention will be apparent from the drawings, discussion and description which follow.

BRIEF DESCRIPTION OF THE INVENTION

There is disclosed herein a sensor system for diagnosing dental conditions. The system is based upon a sensor unit which is configured to be disposed in communication with a user's mouth so as to be contacted by oral fluids such as gas or liquid. The sensor unit is operable to provide detectable signals indicative of the presence of at least two species selected from the group consisting of: hydrogen ion, calcium ion, phosphate ion, sulfur, organosulfur compounds, nitrogen containing compounds, microbial metabolites, and microbes. (It is to be understood that these species may be detected in their ionized or unionized forms, as appropriate.) The system further includes a signal processor in communication with the sensor unit. The signal processor is operative to process the detectable signals and to provide a processed signal indicative of a dental condition. The processor is further operative to transmit the processed signal to a storage and display device which displays a user detectable diagnostic message. In some instances, the sensor is further operative to provide a detectable signal indicative of the concentration of the members of the group. The storage and display unit may comprise a personal digital assistant, computer or the like.

In specific embodiments, the signal processor is operative to transmit the processed signal to the storage and display device via a wireless data link. In yet other embodiments, the sensor unit may be operable to further provide a visual display of the tooth, or a signal indicative of the integrity of the tooth. The diagnostic message displayed by the display device may be indicative of the user's dental condition and/or may suggest a remedial action to the user for the purpose of restoring dental health.

The sensor unit may be configured to be disposed in the user's mouth so as to sense the composition of liquids and/or gases therein. Alternatively, the sensor unit may be disposed external of the user's mouth and be configured to receive exhaled gases from the user.

DETAILED DESCRIPTION OF THE INVENTION

The sensor structures of the present invention are operable to provide detectable signals indicative of at least two different parameters associated with dental health, and in specific embodiments, these detectable signals are provided simultaneously. The detectable signals may be directly, visually detectable. In other instances, the signals will only be visible after subsequent chemical treatment, in which instance they are also characterized as being chemically detectable. In yet other instances, the signals will be electronically detectable. All of such signals are collectively termed detectable.

Figure 1:
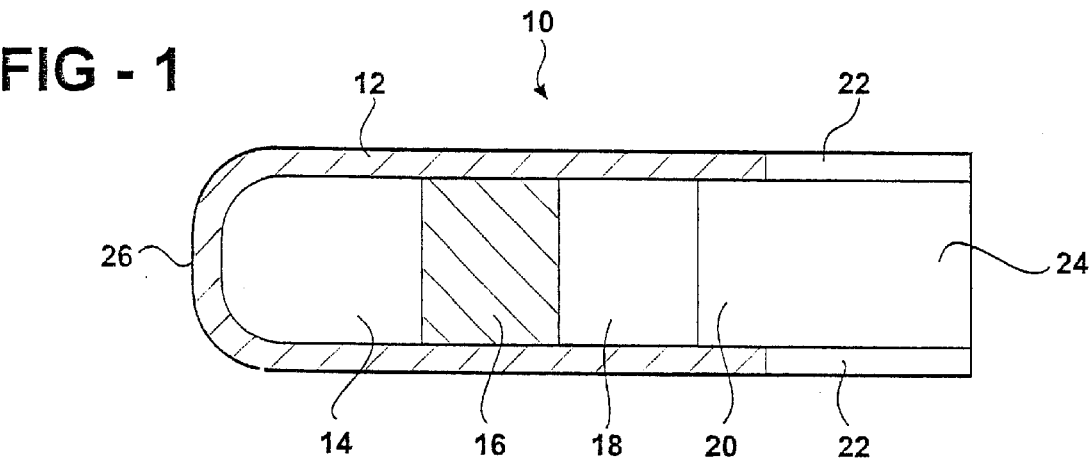
FIG. 1 is a sensor unit of the present invention which is configured in the form of a probe which is placed in a user's mouth.

FIG. 1 shows an elongated sensor structure shown generally at 10, preferably in the shape of a toothpick. The structure 10 has a holding end 24 adapted to be held between the fingers, and a sensing end 26, adapted to be placed in the mouth of a person. The outer surface of the sensing end 26 is formed by a permeable layer 12, which surrounds indicating regions 14, 16, and 18. Indicating regions are adapted to have a visible response to the oral environment. An inert material 20 forms the inner body of the holding end, and is largely surrounded by film 22 which is adapted to assist holding of the sensor structure.

In one particular embodiment, as shown in FIG. 1, indicating region 14 has a visible response to pH, region 16 has a visible response to calcium (either neutral or ionized), and region 18 has a visible response to phosphate ions. In another embodiment regions 14, 16 and 18 have visible responses to different pH ranges, for enhanced sensitivity to pH changes. In another embodiment, one or more indicating regions have a visible response to oral bacteria. In another embodiment, one or more indicating regions have a visible response to the products of oral bacteria, such as sulfur (either neutral or ionized) sulfur-containing compounds (e.g. hydrogen sulfide or organosulfur compounds), nitrogen-containing compounds (such as pyridine derivatives), other organic compounds, and other inorganic compounds. Visible responses include color changes, fluorescence changes, and the like, as viewed in ambient light or under an external radiation source.

Preferably, permeable layer 12 is transparent or translucent. The sensed analyte diffuses through permeable layer. Hence, for pH-induced calorimetric changes of the indicating regions, ions such as hydrogen ions and hydroxyl ions diffuse through the layer 12. In another embodiment, permeable layer 12 may extend over the holding end.

One or more indicating regions may be used. The functionality of indicating regions may be all different, repeated at spatial intervals, or all similar. For example, a periodic pattern of indicating regions would be used to investigate conditions at different locations within the mouth.

In other embodiments, permeable layer 12 and film 22 are omitted, and the structure has form of a plastic toothpick, having a polymeric region near the sensing end providing a visible response to oral conditions, such as pH or the presence of oral bacteria.

Figure 7:
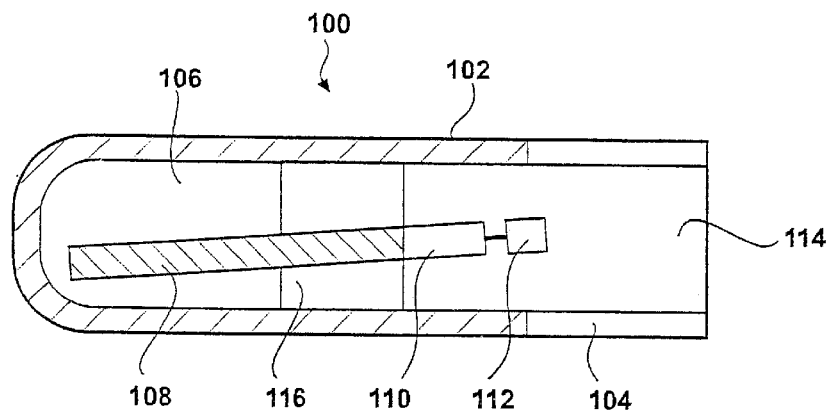
FIG. 7 shows yet another probe which may be used in the present invention.

In one embodiment, the sensing end has a visible response to the presence of S. mutans or other oral bacteria. U.S. Pat. No. 5,492,674 by Meserol, herein incorporated in its entirety by reference, describes the use of an antibody-antigen complex with a fluorescent response. Such techniques are known to those skilled in the art of immunology. FIG. 7 shows a structure 100 adapted to provide a visible response to oral bacteria. Fluorescent indicating region 106 is formed around a central cylindrical fiber 108. The structure 100 has a radiation source 110, preferably a light emitting diode, powered by a battery 112. Membrane 102 covers the fluorescent indicating region, and is permeable to S. mutans. Film 104 assists grip of the holding end. Regions 116 and 114 are inert regions, providing mechanical strength. Radiation from the source 110 passes along fiber 108 and excites the fluorescent indicating region 106. Region 106 is adapted to provide a fluorescent response to oral bacteria, using techniques known in the immunological arts. A switch, such as a pressure sensitive switch activated by holding the structure 100, may be provided to control the application of power to source 110. In another embodiment, fiber 108 is extended through the region 114, so as to allow the exciting radiation to be provided externally, allowing the battery and source to be absent from structure 100. In another embodiment, fiber 108 is replaced by a cavity.

Other embodiments of the present invention may be used to detect the acidity, ion levels, and bacteria content of saliva samples extracted from the mouth, for example into a capillary tube lined with an indicating medium, or saliva sucked from around the base and gaps between teeth.

Figure 2:
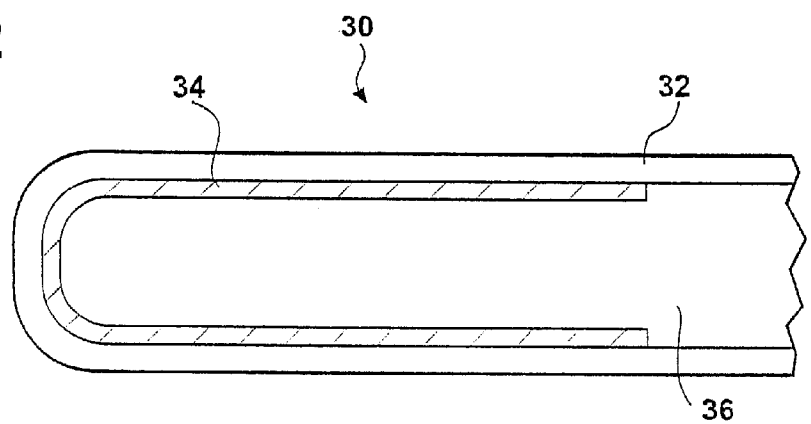
FIG. 2 is a depiction of a portion of another embodiment of sensor of the present invention configured to be placed within a user's mouth.

FIG. 2 shows the sensing end of another embodiment 30. This has a permeable layer 32, a pH-sensitive colorimetric response layer 34, and an inert rigid or flexible core 36. A core such as 36 may be used to transmit light from a light source nearer the holding end, so as to excite fluorescence or illuminate a calorimetric response region.

Figure 3:
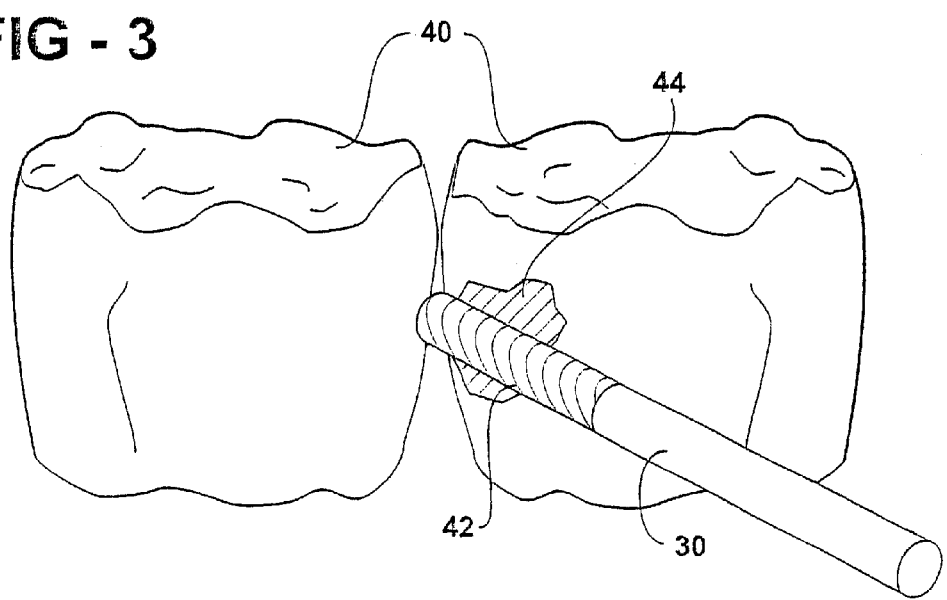
FIG. 3 shows the probe of FIG. 2 in one mode of use.

In use the structure (e.g. 10, 30, or 100) is placed into the mouth so that the sensing end is exposed to oral environment. FIG. 3 shows structure 30 placed against teeth 40 of the person. Saliva droplets 44 contact the sensing end 42 of the structure 30. A color response of the sensing end 42 is preferably used to indicate acidic levels of pH of the saliva. For example, the sensing end of the structure may turn from colorless to red in the presence of an acidic environment. This warns the user that conditions exist favorable for the formation of dental caries.

A color response to ion levels in the saliva is useful in preventing dental caries. A certain minimum level of calcium and phosphate ions in the saliva is desirable to assist in the remineralization of enamel between meals. If no indication of calcium ions or phosphate ions is shown using such a structure, the user would be advised take action, e.g. chewing appropriate gum, using mouthwash, applying gels, etc., to enhance the levels of these ions. Such formulations are known in the dental care art, and may contain for example calcium phosphate, calcium stearate, and other calcium-containing compounds or phosphate-containing compounds. Fluoride ions are also known to assist in enamel remineralization, so indicating regions for fluoride ions may also be used, or fluoride-containing formulations can be used. In other embodiments, the sensing end contains reference regions not exposed to the oral environment to assist the quantitative determination of pH or other ion levels from the visible response.

Preferably, the visible response chemistry used in the indicating regions does not diffuse out of the permeable membrane. Preferably, the visible response chemistry is nontoxic. A polymeric material is advantageous, in which molecular moieties providing the visible response are covalently attached to a polymer backbone.

Figure 4:
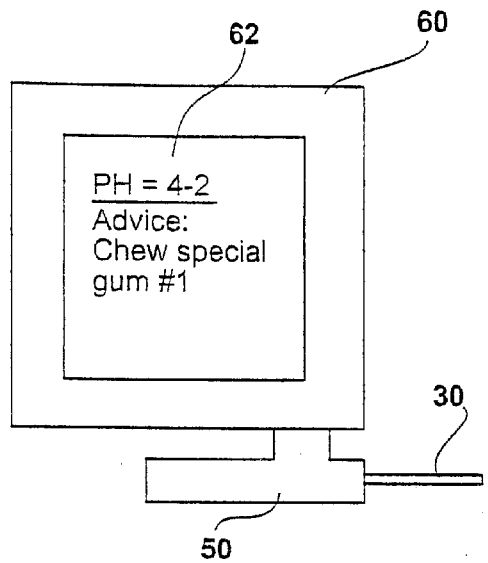
FIG. 4 shows the probe of FIG. 2 being read by a signal processor.

FIG. 4 shows the structure 30 placed into a reading device 50 which is a plug-in accessory to a personal digital assistant (PDA) 60. The reading device analyzes the visible response of the structure to the oral environment, and provides data such as pH which is communicated to software running on the PDA. The display 62 of PDA 60 is used to provide feedback to the person, for example to prompt the user to clean teeth, chew gum, use mouthwash, etc. The term PDA refers to any portable device with computing capability and a display (or other method to transmit information to a user), such as a portable computer, pager, e-book, wireless phone, and the like.

Figure 5:
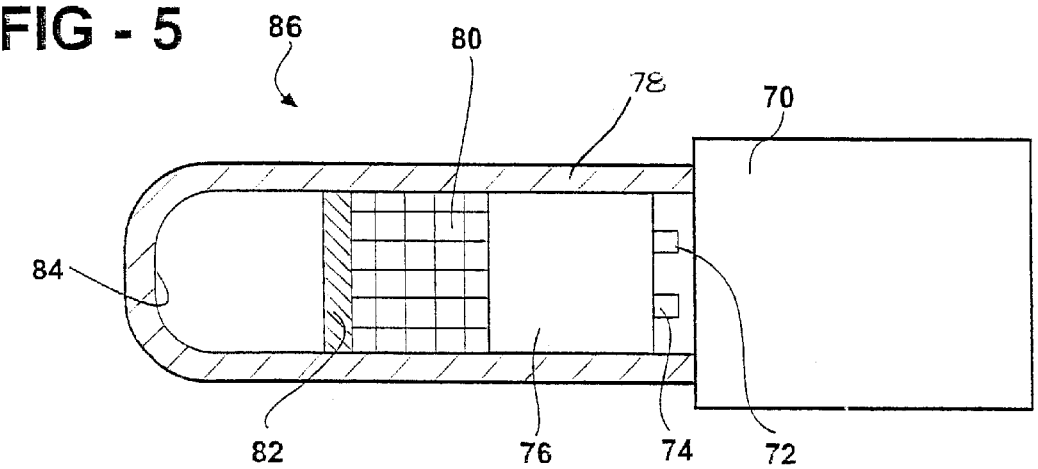
FIG. 5 is a depiction of another embodiment of the present invention comprised of a sensor unit having a signal processor integral therewith.

FIG. 5 shows another embodiment. A disposable sensor structure is formed from outer membrane 78, transparent medium 76, indicating region 80, and a reflector 82. Disposable sensor 86 makes an optical interface with an electronic analysis device 70. This device provides a radiation source 72 and radiation detector 74. Disposable sensor 86 is placed in the mouth. Radiation emitted from source 72 in the analysis device is reflected by reflector 82 back to detector 74. Radiation levels received by detector 74 are changed due to the visible response of indicating region 80 to the oral environment, for example saliva pH. The radiation level at the detector will increase or decrease depending on the radiation wavelength and exact nature of the visible response of the indicating region to the oral environment. A color filter may be placed in front of the detector and/or radiation source. The reflector 82 is optional, as the radiation may also be reflected from the inner curved surface 84 of the membrane 78.

Analysis circuitry within device 70 allows determination of the pH value based on the response of the detector. The pH may be shown on a display mounted on the housing, or transmitted to a PDA for display. Device 70 may be an accessory module for a PDA, such as plug-in module, in which case the display of the PDA may be used to display the measured pH and any relevant feedback.

Optical fibers, preferably plastic fibers, may also be used to transmit radiation to the sensing end of the pH indicating structure, and carry back reflected or scattered radiation to the detector.

Figure 6:
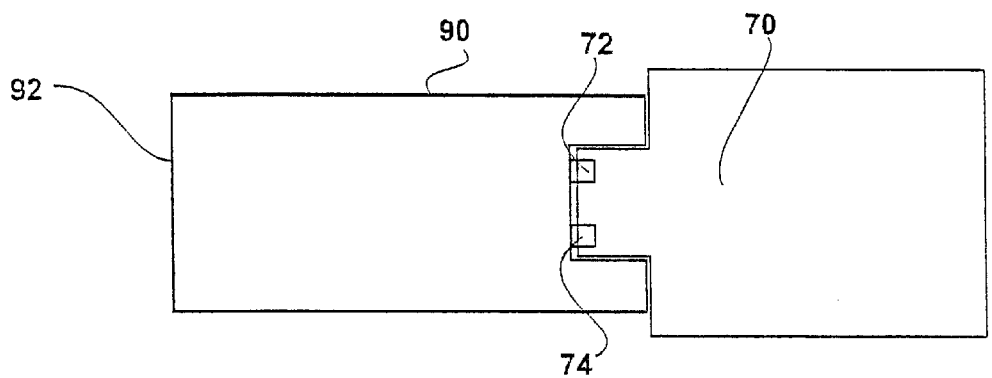
FIG. 6 depicts yet another embodiment of the present invention having an oral probe.

FIG. 6 shows another embodiment of the invention. Electronic analysis device 70 provides a radiation source 72 and radiation detector 74. Device 70 makes optical and mechanical connection to a plastic fiber 90. Radiation emitted by radiation source 72 is reflected by the end of the fiber 92 back to the detector 70. Preferably, the fiber is made from an optical plastic containing a pH indicator, which provides a visible response to ions diffusing into the fiber material. Preferably, the pH indicator is a non-toxic polymer. In one embodiment, the fiber 90 has a porous (or permeable) indicating region near the end 92, with the visible response provided by an indicating chemistry within the indicating region. In another embodiment, the fiber may also have a fluorescent response to ions or bacteria in the saliva. The fiber may also contain radiation reflectors, optical filters, dyes, or other optical elements. The fiber is placed in the mouth, and the reflected radiation detected. Radiation emission and detection of two different wavelengths may also be used to more accurately determine the color response of the indicating chemistry, as the ratio of attenuation at two or more suitable wavelengths is a sensitive method of determining pH change from calorimetric pH indicators.

In U.S. Pat. No. 5,188,109, Saito describes an artificial dental root for physiological monitoring. Such a device may also be adapted for saliva monitoring. However, it is not necessary to provide a dental root for oral environment monitoring. An artificial crown, or cap, may be provided containing pH sensing chemistry or electronic devices. The device may be powered by a piezoelectric crystal, for example by chewing or by a radiation source, or by ambient electromagnetic radiation such as is found at the frequency of mains electricity, or by using one or more radio station transmissions. The dental crown or cap may have additional functionality. For example, the device may be used to detect sugar content of foods, chewing motion, and other diet-related parameters. Using an oscillating piezoelectric crystal within the dental crown, feedback may be provided by the mechanical coupling between the tooth and the inner ear of the person. For example, a person might hear a voice inside their head saying "stop eating now" if sugar is detected over a long time period, or if chewing is prolonged. The adapted crown may also convert wireless transmissions, e.g. from a PDA, into a signal audible to the person.

The crown-based sensor may also be provided with functionality to communicate with a PDA. For example, a person may bring a PDA close to the mouth. The dental crown may be in wireless communication with a PDA, so that the PDA can communicate with the user by vibrations of the crown. Radiation from the PDA may power the sensor transmitter in the tooth crown. Sensors within the crown measure the pH of the saliva, and the value is transmitted back to the PDA. The PDA is then used to provide feedback to the person. The crown sensor may also contain ultrasonic transducers which probe the density of the tooth and surrounding bone.

Figure 8:
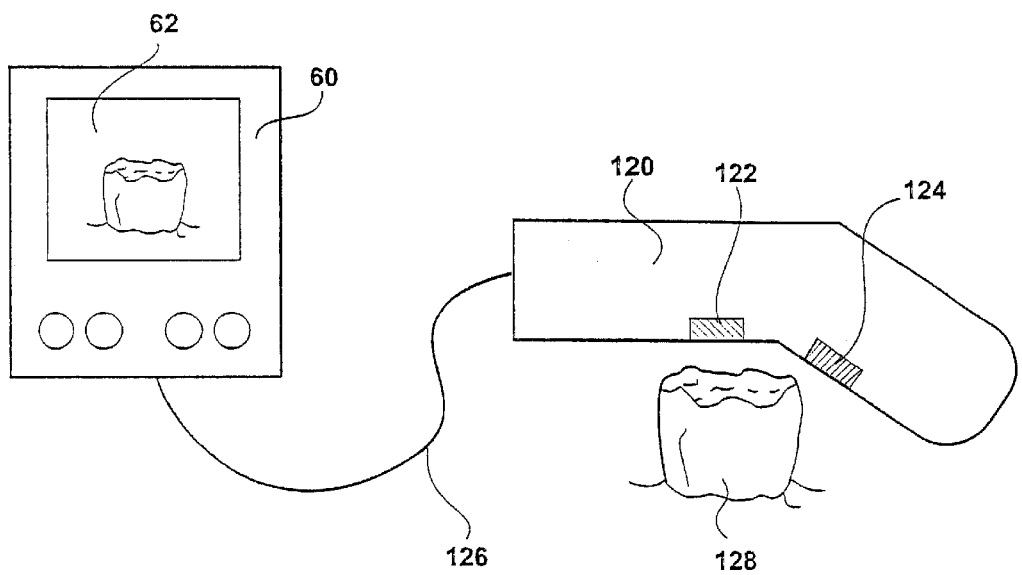
FIG. 8 shows an embodiment of the present invention wherein a sensor probe is coupled to a PDA.
Figure 9:
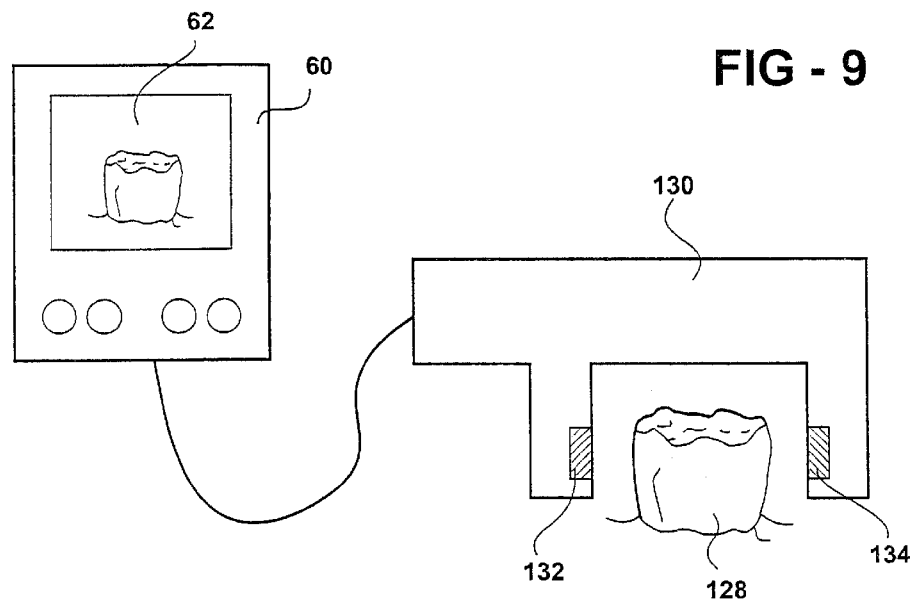
FIG. 9 shows another embodiment of the present invention wherein a sensor probe including an ultrasonic imaging device is coupled to a PDA.

An accessory to a PDA (personal digital assistant) or other computing device may be used to form images of the teeth and display them conveniently to the user. FIG. 8 shows a PDA 60 with display 62 connected using cable 126 to a handheld probe 120. Optical imaging of teeth is performed using probe 120 having an optical image sensor 124 and light source 122. The image of tooth 128 is shown on the PDA display 62. In an alternative embodiment, the probe may transmit image data using wireless methods, such as the Bluetooth wireless protocol. An array of optical fibers may also be used in imaging. A person may rinse first with known formulations that enhance the visibility of plaque deposits, for example by staining (e.g. as described by Yamauchi in U.S. Pat. No. 4,347,233, and Kowalyk in U.S. Pat. No. 5,456,603). Fluorescent imaging of teeth may indicate regions of possible decay, as is known in the dental arts. In the fluorescent imaging embodiment, light source 124 is preferably a blue or UV light emitting diode. FIG. 9 shows a PDA 60 with display 62 connected using cable 126 to a handheld ultrasonic imaging device 130. Device 130 provides micromachined ultrasonic transducer arrays 132 and 134, which are used for imaging teeth and detecting decay. Attenuation, transit time, and broadband spectral response images of tooth 128 are shown on PDA display 62. An advantage of this embodiment is that the computing power and display of the PDA are used in dental diagnosis.

Figure 10:
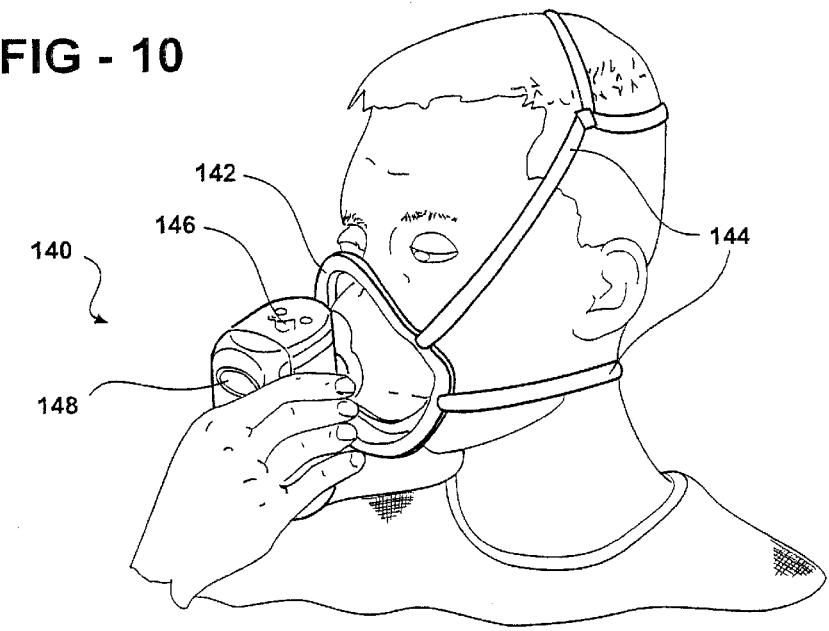
FIG. 10 shows an embodiment of the present invention as configured to sense a gaseous fluid stream.

FIG. 10 shows a person breathing through a respiratory analyzer (such as an indirect calorimeter or a spirometer) shown generally at 140, having a respiratory connector in the form of a mask 142. Optional straps 144 or a hand are used to hold the mask against the face. A button 146 is used to initial a testing cycle. A display 148 is used to display data to the user. In another embodiment, a mouthpiece and nose clip are used instead of the mask to exclude air from the sinuses. An indirect calorimeter used in a preferred embodiment is fully described in a co-pending application to James R. Mault, M.D., Ser. No. 09/630,398. Exhaled air passing through the flow path of the respiratory analyzer is analyzed to diagnose the oral condition. In one embodiment, the exhaled air passes over a sensor for *S. mutans*, preferably a fluorescent sensor. In another embodiment, a pH sensor, preferably a fluorescent sensor, is located in the flow path so as to detect acidic components of the breath. Oral-related breath acidity is determined using the response to the initial component of exhaled air, which may be termed "mouth air".

This provides a method of diagnosing an oral condition for a person, comprising of having the user exhale through a flow path, so that exhaled breath flows over fluorescence sensor adapted to provide a response correlated with the presence of acidic components in exhaled breath. Hence acidic components of the exhaled breath (such as lactic acid traces in water droplets, and other components) are qualitatively or quantitively determined, so as to provide a diagnosis of oral condition.

Exhaled air contains a mixture of organic and inorganic trace gases, such as pentane, hydrogen sulfide, and others which are known in the art. The complex signature of such trace gases in the first component of exhalation (oral-related breath, or mouth breath) is diagnostic of oral conditions. Hence, determination of the ratio of concentrations of two gases in the exhaled air, such as hydrogen sulfide and ammonia, may be used to provide an indication of the oral condition, such as saliva pH. Shallow, frequent breaths are advantageous in respiratory oral diagnosis. Saliva pH influences the bacterial population distribution in the mouth, and hence detection of bacterial byproducts in exhaled breath can be used to determine oral acidity, and other indicators of oral health.

Stomach bacteria such as *Helicobacter pylori* may also be detected in exhaled air, particularly if belching is induced, using fluorescent sensors in the flow path of a respiratory analyzer. The use of (for example) immunological fluorescent sensors to *H. pylori* is simpler than the detection method disclosed by Katzmann in U.S. Pat. No. 6,067,989.

Periodontal disease may be diagnosed using the detection of compounds such as pyridine, alkyl-pyridines, hydrogen sulfide, ammonia, urea, thiols, and other sulfur and/or nitrogen containing compounds, as described by Preti in U.S. Pat. No. 4,334,540, herein incorporated by reference. Hence, embodiments of the present invention sensitive to such compounds are useful in the early detection of periodontal disease. A sensitive colorimetric response in the sensing end of a structure such as 10 may be used to indicate diagnostic levels of hydrogen sulfide in the saliva. An immunological response to bacteria related to periodontal disease may also be used, for example a fluorescent detection method. Respiration analysis may be used to detect compounds diagnostic of periodontal disease. A colorimetric, fluorescent, micromachined, or other gas sensor may be provided in the flow path of a respiratory analyzer, such as a spirometer, indirect calorimeter, or other analytic instrument. Ultrasonic transducers may be used to determine flow rates and breath flow profiles. The origin of breath components is assisted by knowing the time in the breath higher concentrations occur. For example, oral origin gases occur early in an exhalation.

Yet other embodiments and variations of the present invention will be readily apparent to one of skill in the art in view of the teaching presented herein. The drawings, discussion and description are illustrative of specific embodiments of the present invention, but are not meant to be limitations upon the practice thereof. It is the following claims, including all equivalents, which define the scope of the invention.

What is claimed is:

1. A sensor system for diagnosing dental conditions comprising:

a sensor unit configured to be disposed in communication with a user's mouth so as to contact an oral fluid, said sensor unit being operative to provide detectable signals indicative of the presence of at least two species selected from the group consisting of: hydrogen ion, calcium, phosphate, sulfur, sulfur containing compounds, nitrogen containing compounds, microbial metabolites, and microbes; and a signal processor in communication with the sensor unit, said signal processor being operative to process said detectable signals and to provide a processed signal indicative of a dental condition, said signal processor being further operative to transmit said processed signal to a storage and display device which displays a user detectable diagnostic message.

2. The sensor system of claim 1, wherein said sensor unit is configured to be disposed within a user's mouth.

3. The sensor system of claim 2, wherein said oral fluid comprises saliva.

4. The sensor system of claim 1, wherein said oral fluid comprises a gas.

5. The sensor system of claim 4, wherein said sensor unit is configured to be disposed externally of the user's mouth.

6. The sensor system of claim 1, wherein at least one of said detectable signals is indicative of the concentration of at least one of said species.

7. The sensor system of claim 1, wherein said storage and display device comprises a personal digital assistant.

8. The sensor system of claim 1, wherein said storage and display device comprises a computer.

9. The sensor system of claim 1, wherein said signal processor comprises a personal digital assistant.

10. The sensor system of claim 1, wherein said signal processor comprises a computer.

11. The sensor system of claim 1, wherein said signal processor is operative to transmit said processed signal to said storage and display device through a wireless data link.

12. The sensor system of claim 1, wherein said system is further operative to provide a visual display of a user's tooth.

13. The sensor system of claim 1, wherein said sensor system is operable to provide a user detectable display indicative of the integrity of a user's tooth.

14. The sensor system of claim 1, wherein said user detectable diagnostic message is indicative of a dental condition.

15. The sensor system of claim 1, wherein said user detectable diagnostic message comprises a message directing the user to take a particular remedial action.

16. The sensor system of claim 1, wherein said signal processor is external of the user's mouth.

17. A sensor system for diagnosing dental conditions, said sensor comprising:

a sensor unit configured to be disposed in communication with a user's mouth so as to contact an oral fluid, said sensor unit operative to provide detectable signals indicative of the presence in said oral fluid of at least two species selected from the group consisting of hydrogen ion, calcium, phosphate, sulfur, sulfur containing compounds, nitrogen containing compounds, microbial metabolites, and microbes.

18. The sensor system of claim 17, wherein at least one of said detectable signals is a visually detectable signal.

19. The sensor of claim 17, wherein at least one of said detectable signals is an electronically detectable signal.

20. The sensor system of claim 17, wherein at least one of said detectable signals is a chemically detectable signal.

21. The sensor system of claim 17, wherein said sensor unit is configured to contact a gaseous oral fluid and to provide detectable signals indicative of the presence of said at least two species in said gaseous oral fluid.

22. The sensor system of claim 17, wherein said sensor unit is configured to contact saliva and to provide detectable signals indicative of the presence of said at least two species in said saliva.

23. The sensor system of claim 17, further including a signal processor in communication with said sensor unit, said signal processor being operative to process said detectable signals and to provide a processed signal indicative of a dental condition.

24. The sensor system of claim 23, wherein said signal processor is further operative to transmit said processed signal to a storage and display device which displays a user detectable diagnostic message.

25. The sensor system of claim 17, wherein at least one of said detectable signals is indicative of the concentration of at least one of said species.

26. A method for diagnosing a dental condition, said method comprising the steps of:

providing a sensor unit operative to contact an oral fluid and to provide detectable signals indicative of the presence of at least two species selected from the group consisting of: hydrogen ion, calcium, phosphate, sulfur, sulfur containing compounds, nitrogen containing compounds, microbial metabolites, and microbes;

disposing said sensor unit in contact with an oral fluid, whereby said sensor unit provides said detectable signals;

communicating said detectable signals to a signal processor which is operative to process said detectable signals and provide a processed signal indicative of a dental condition.

27. The method of claims 26, including the further step of:

transmitting said processed signal to a storage and display device which displays a user detectable diagnostic message.

* * * * *